United States Patent
Song et al.

(10) Patent No.: US 9,689,937 B2
(45) Date of Patent: Jun. 27, 2017

(54) NON-RESONANT MAGNETIC RESONANCE TRANSMITTER WITH POWER FACTOR CORRECTION

(71) Applicant: SCHLUMBERGER TECHNOLOGY CORPORATION, Sugar Land, TX (US)

(72) Inventors: Yi-Qiao Song, Newton, MA (US); Soumyajit Mandal, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 658 days.

(21) Appl. No.: 14/067,567

(22) Filed: Oct. 30, 2013

(65) Prior Publication Data
US 2015/0115954 A1 Apr. 30, 2015

(51) Int. Cl.
G01R 33/34 (2006.01)
G01V 3/08 (2006.01)
G01V 3/32 (2006.01)
G01R 33/36 (2006.01)
G01N 24/08 (2006.01)

(52) U.S. Cl.
CPC ... *G01R 33/34092* (2013.01); *G01R 33/3607* (2013.01); *G01R 33/3614* (2013.01); *G01V 3/32* (2013.01); *G01N 24/081* (2013.01); *G01R 33/34053* (2013.01)

(58) Field of Classification Search
CPC .......... G01R 33/34092; G01R 33/3614; G01R 33/3607; G01R 33/34053; G01V 3/32; G01N 24/081

USPC .......................................................... 324/303
See application file for complete search history.

(56) References Cited

U.S. PATENT DOCUMENTS

| | | | |
|---|---|---|---|
| 4,628,264 A | 12/1986 | Rzedzian | |
| 5,629,623 A | 5/1997 | Sezginer et al. | |
| 5,804,967 A * | 9/1998 | Miller | G01R 33/441 324/307 |
| 6,392,410 B2 | 5/2002 | Luong et al. | |
| 6,774,628 B2 * | 8/2004 | Ganesan | G01V 3/32 324/303 |

(Continued)

OTHER PUBLICATIONS

U.S. Appl. No. 13/963,826, "Magnetic Resonance Transmitter," filed Aug. 9, 2013: pp. 1-18.

(Continued)

*Primary Examiner* — Melissa Koval
*Assistant Examiner* — Rahul Maini
(74) *Attorney, Agent, or Firm* — Bridget M. Laffey

(57) ABSTRACT

A non-resonant transmitter for a magnetic resonance (MR) system, such as a nuclear magnetic resonance (NMR) system, is described herein. The transmitter includes a coil for applying NMR pulse sequences to a substance. The coil is coupled to a circuit that includes a capacitor, a number of switches, and a power source. The transmitter operates in two modes. In a charging mode, the switches decouple the coil from the capacitor and the capacitor is charged by the power source. In a discharging mode, a radio frequency pulse is generated and the switches couple and decouple the coil from the capacitor so that the capacitor provides power to the coil. The addition of the capacitor improves the power factor of the circuit and reduces power draw from the power source.

19 Claims, 10 Drawing Sheets

(56) References Cited

U.S. PATENT DOCUMENTS

| | | |
|---|---|---|
| 8,164,336 B1 | 4/2012 | Murphree, Jr. et al. |
| 2004/0066194 A1* | 4/2004 | Slade ........................ G01V 3/32 |
| | | 324/318 |
| 2012/0001629 A1* | 1/2012 | Hopper .................... G01V 3/32 |
| | | 324/303 |
| 2013/0234705 A1 | 9/2013 | Mandal et al. |

OTHER PUBLICATIONS

Hopper et al., "Low-frequency NMR with a non-resonant circuit," Journal of Magnetic Resonance, 2011, vol. 210(1): pp. 69-74.
Scott et al., "Utility of a tuneless plug and play transmission line probe," Journal of Magnetic Resonance, 2012, vol. 221: pp. 117-119.

\* cited by examiner

US 9,689,937 B2

NON-RESONANT MAGNETIC RESONANCE TRANSMITTER WITH POWER FACTOR CORRECTION

TECHNICAL FIELD

This disclosure relates to magnetic resonance (MR) systems, and more particularly to MR transmitters.

BACKGROUND

Magnetic resonance (MR) systems can be used to determine properties of a substance. One example of a MR system is a nuclear magnetic resonance (NMR) system. A NMR system performs a NMR measurement by applying a static magnetic field to the substance. The static magnetic field generates an initial magnetization of atomic nuclei within the substance. The NMR system also includes a NMR transmitter with a coil that applies an oscillating magnetic field at a particular "Larmor" frequency to the substance. The oscillating field is composed of a sequence of radio frequency pulses that tip the magnetization of the atomic nuclei away from the initial magnetization. This sequence is also known as a NMR pulse sequence. The NMR pulse sequence can be arranged so that pulses and the static field interact with the nuclei to produce a resonant signal composed of "echoes" within at least a portion of the substance. The resonant signal is detected and then used to determine NMR properties such as $T_1$ relaxation time, $T_2$ relaxation time, and attenuation of the signal due to molecular diffusion. These NMR properties can be used to determine the properties of the substance.

In a narrowband NMR transmitter, the coil is tuned to a particular Larmor frequency of interest using a capacitor that is coupled to the coil. The particular frequency that is transmitted by the coil can be determined according to the following relationship:

$$f = \frac{1}{2\pi\sqrt{LC}}, \quad (1)$$

where f is the particular frequency, L is the inductance of the coil, and C is the capacitance of the capacitor.

In some cases, the NMR pulse sequences are applied to the substance at different frequencies to investigate different portions of a substance in an inhomogeneous magnetic field or to investigate atomic nuclei with different Larmor frequencies. To switch between frequencies, narrowband NMR transmitters use banks of fixed capacitors and mechanical switches that are coupled to the coil. The mechanical switches tune the coil to different frequencies by switching between a pre-set number of fixed capacitors. These narrowband transmitters suffer from several disadvantages. Firstly, the switching process is slow (e.g., 10-100 ms switching times). Secondly, the switches within the capacitor banks introduce noise into the NMR measurement. Thirdly, a predetermined discrete set of narrowband frequencies can be set because each frequency is dependent on separate capacitors. Fourthly, the frequency switching process introduces dynamics and may not maintain phase coherence of the pulse sequence waveform. Accordingly, narrowband NMR transmitters do not efficiently and effectively switch between frequencies.

SUMMARY

Illustrative embodiments of the present disclosure are directed to a transmitter for a magnetic resonance (MR) system, such as nuclear magnetic resonance (NMR) system. The transmitter includes a coil for applying NMR pulse sequences to a substance. The coil is coupled to a circuit that includes a capacitor, a number of switches, and a power source. The power source is coupled to the capacitor. In turn, the capacitor is selectively coupled to the coil using the switches.

In some embodiments, the transmitter operates in two modes. In a charging mode, the switches decouple the coil from the capacitor and the capacitor is charged by the power source. In a discharging mode, the switches couple and decouple the coil with the capacitor so that the capacitor provides power to the coil and generates a radio frequency pulse.

Various embodiments of the present disclosure are also directed to a non-resonant MR device for transmitting radio frequency pulses. The device includes a coil for transmitting the radio frequency pulses and a circuit for powering the coil. The circuit includes a capacitor arranged in parallel with the coil and a number of transistors coupled between the capacitor and the coil. The transistors selectively couple the coil to the capacitor. The circuit includes a power source coupled to the capacitor and that charges the capacitor. In turn, the capacitor powers the coil when the transistors couple the coil to the capacitor.

Further embodiments of the present disclosure are directed to a method for transmitting radio frequency pulses. The method includes (i) decoupling a capacitor from a coil to charge the capacitor over a first time period and (ii) coupling and decoupling the capacitor with the coil to generate a radio frequency pulse over a second time period. In illustrative embodiments, the coupling and decoupling in process (ii) may be repeated a number of times to generate the radio frequency pulse over the second time period. Furthermore, processes (i) and (ii) may be repeated a number of times to generate many radio frequency pulses that are each separated from adjacent pulse by the first time period.

BRIEF DESCRIPTION OF THE DRAWINGS

Those skilled in the art should more fully appreciate advantages of various embodiments of the disclosure from the following "Description of Illustrative Embodiments," discussed with reference to the drawings summarized immediately below.

DESCRIPTION OF ILLUSTRATIVE EMBODIMENTS

Illustrative embodiments of the present disclosure are directed to a non-resonant transmitter for a magnetic resonance (MR) system, such as nuclear magnetic resonance (NMR) system. The non-resonant transmitter includes a coil for transmitting radio frequency pulses. The coil is coupled to a circuit that includes a capacitor, a number of switches, and a power source. The switches selectively couple the coil to the capacitor. In a charging mode, the switches decouple the coil from the capacitor and the capacitor is charged by the power source. In a discharging mode, the switches couple and decouple the coil with the capacitor to provide power from the capacitor to the coil. By rapidly turning the switches "on" and "off" in the discharging mode, the circuit produces a waveform of a given frequency that is provided to the coil to generate radio frequency pulses. The frequency of the waveform can be modulated by operation of the switches. In this manner, various embodiments of the non-resonant transmitter are able to transmit radio frequency pulses over a wide frequency range, while the addition of the capacitor improves the power factor of the circuit and reduces power draw from the power source. Details of various embodiments are discussed below.

Figure 1:
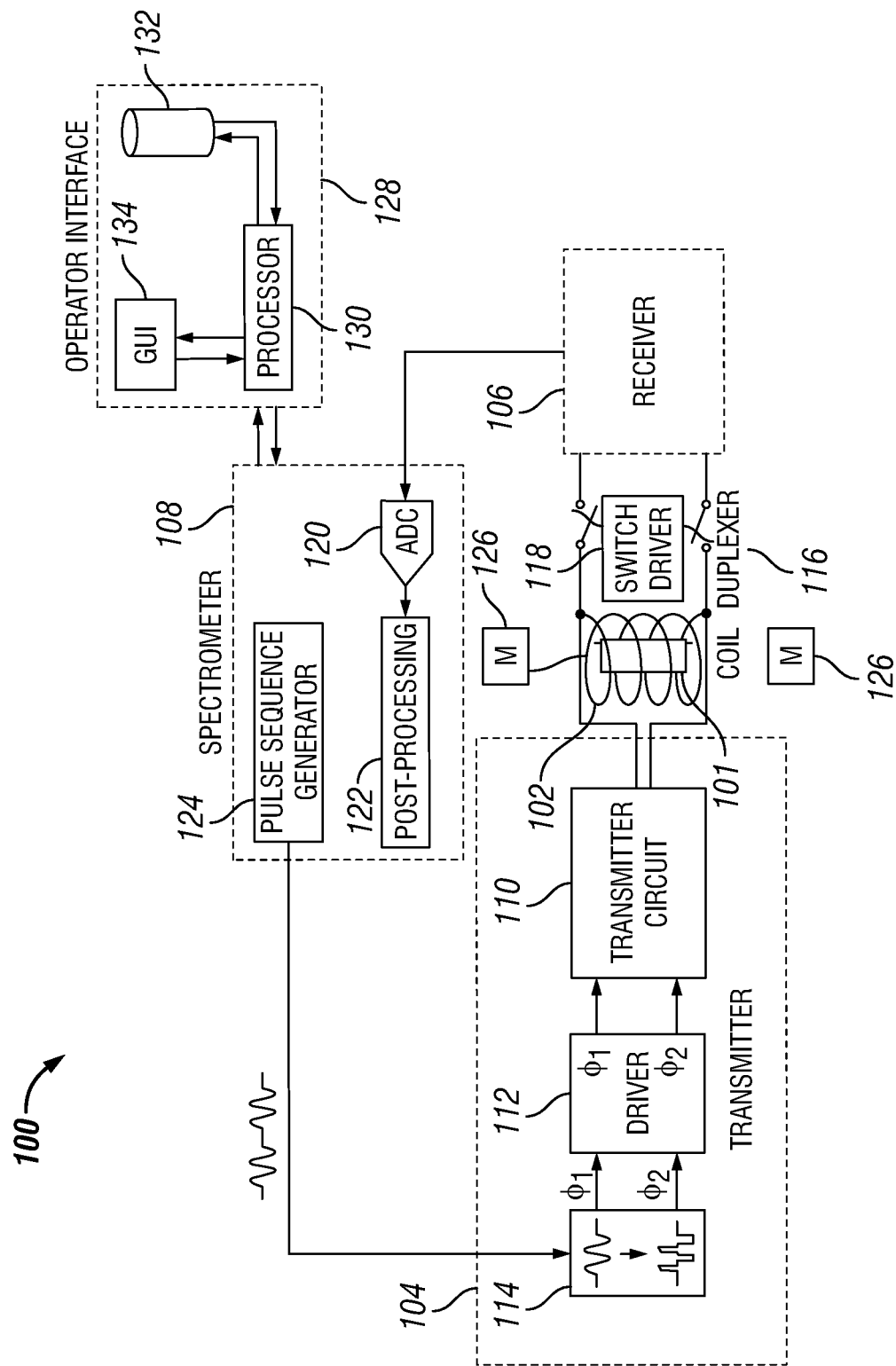
FIG. 1 shows a NMR system in accordance with one embodiment of the present disclosure.

FIG. 1 shows a NMR system 100 in accordance with one embodiment of the present disclosure. The NMR system 100 includes a coil 102 that is coupled to NMR electronics 104, 106, 108. A sample substance 101 is located inside and/or outside of the coil 102. The coil 102 applies radio frequency pulses and NMR pulse sequences to the substance 101. The NMR electronics include a transmitter 104 and a receiver 106. Each of the transmitter 104 and the receiver 106 are coupled to the coil 102. In some embodiments, however, the NMR system 100 may include separate transmitter and receiver coils.

The NMR transmitter 104 also includes a non-resonant transmitter circuit 110 that is coupled to the coil 102. The transmitter circuit 110 generates radio frequency pulses and NMR pulse sequences. These pulses and sequences are then provided to the coil 102. The transmitter circuit 110 is "non-resonant" because the resonant frequency of the circuit does not need to match the Larmor frequency of interest. In contrast, as explained above, narrow-band circuits are set to resonant frequencies that match the Larmor frequency of interest by selecting a capacitor with a particular capacitance for the circuit, according to equation 1 above.

Figure 2:
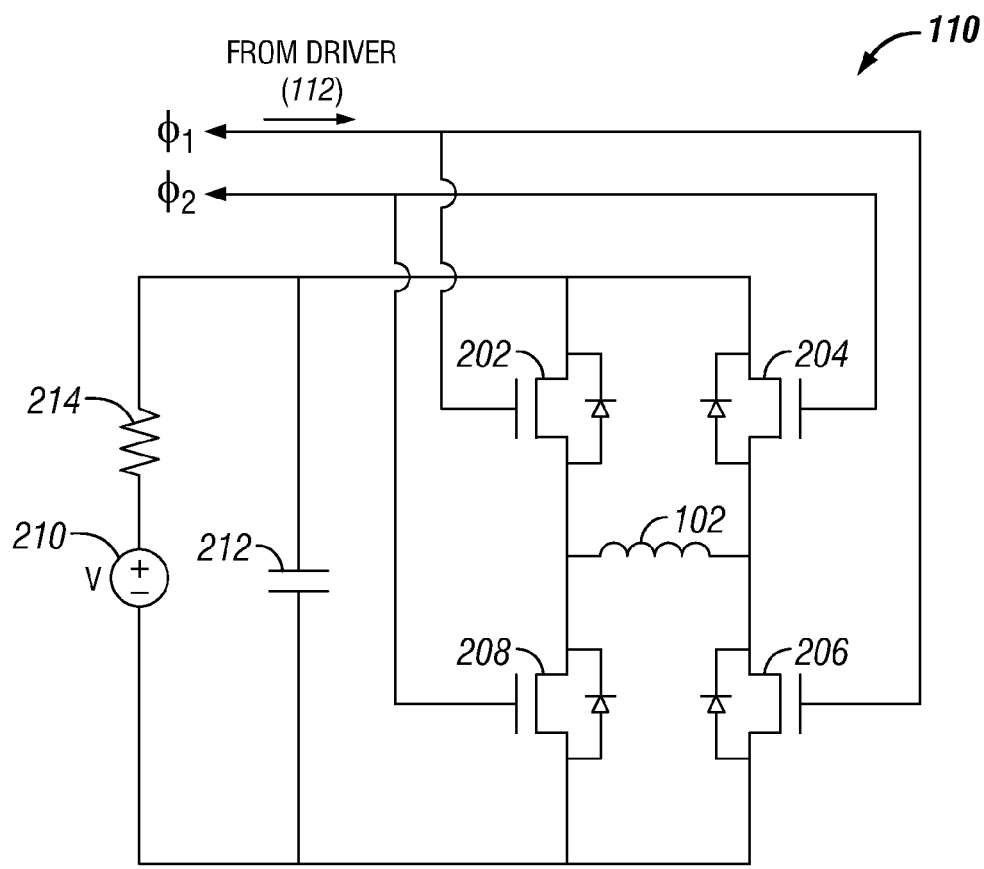
FIG. 2 shows a transmitter circuit in accordance with one embodiment of the present disclosure.

FIG. 2 shows a non-resonant transmitter circuit 110 in accordance with one embodiment of the present disclosure. The transmitter circuit 110 includes two loops. A first loop includes a power source 210, a capacitor 212, and a resistor 214. The power source can be a DC power supply, such as a battery. In various embodiments, a range of voltage applied by the power source 210 can be 1 V (for small coils) and 10,000 V (for large coils or high power applications). The capacitor 212 corrects the power factor of the transmitter circuit 110, as further described below. A second loop includes the capacitor 212 arranged in parallel with a coil 102. In illustrative embodiments, depending on coil size and Larmor frequency, the capacitor 212 has a capacitance between 1 pF and 100 μF. The second loop also includes a number of switches 202, 204, 206, 208 (one or more switches) that are coupled between the capacitor 212 and the coil 102. The capacitor 212 is selectively coupled to the coil 102 via the switches 202, 204, 206, 208. The switches 202, 204, 206, 208 couple the capacitor 212 and the coil 102 by allowing current to pass in an "on" position and decouple the capacitor and the coil by halting current flow in an "off" position. The switches 202, 204, 206, 208 "selectively" couple and decouple the capacitor 212 and the coil 102 according to a control signal, such as the switching logic described below. The switches 202, 204, 206, 208 are arranged in a circuit known as an H-bridge. The switches 202, 204, 206, 208 control the timing and the direction of the current flow in the coil 102. In one particular embodiment, the switches 202, 204, 206, 208 are transistors, such as metal-oxide-semiconductor field-effect transistors (MOSFET), insulated gate bi-polar transistors (IGBT), or various other switches based upon the high frequency switching (HFS) family. In various embodiments, the switches can switch at less than 10 ns.

As explained above, the non-resonant transmitter circuit 110 may also include a resistor 214. The resistor 214 can be used in series with the power source 210 to limit the current applied to the switches 202, 204, 206, 208 and/or to adjust a charging time constant for the capacitor 212. For example, the resistor 214 can be used to increase the charging time constant of the capacitor 212 and, thus, to limit charging of the capacitor during a discharging mode of the transmitter circuit 110. In various embodiments, the resistor 214 has a resistance between 0.1 ohms to 5 ohms.

The non-resonant transmitter circuit 110 operates in a charging mode and a discharging mode. In the charging mode, the switches 202, 204, 206, 208 are "off" and the coil 102 is decoupled from the capacitor 212 for a charging time period. The power source 210 charges the capacitor 212 by providing current to the capacitor 212. In the discharging mode, the switches 202, 204, 206, 208 selectively power the coil 102 by allowing current to pass to the coil from the capacitor 212. In this mode, the switches 202, 204, 206, 208 selectively couple and decouple the coil 102 with the capacitor 212 over a discharging time period by rapidly switching between "on" and "off" positions. By selectively coupling and decoupling the coil 102 with the capacitor 212, the switches 202, 204, 206, 208 control the direction and timing of current flow within the coil. Turning these switches "on" and "off" using a certain switching logic generates a waveform of current in the coil 102 that produces radio frequency irradiation. In this manner, the operation of the switches 202, 204, 206, 208 generates a radio frequency pulse and an NMR pulse sequence.

Figure 3:
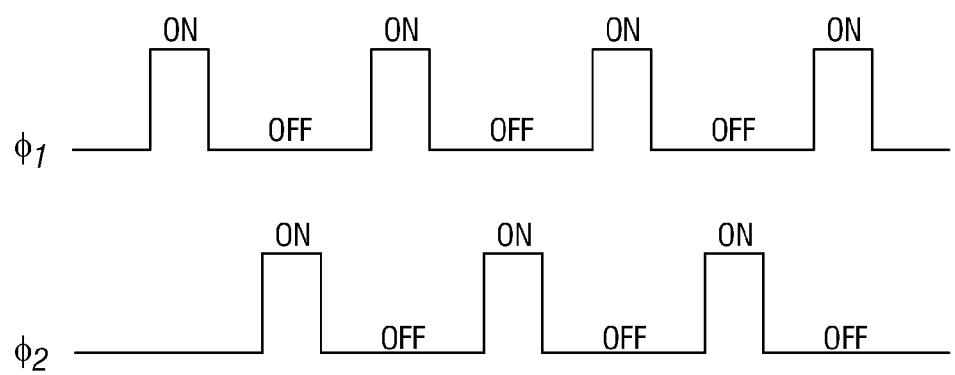
FIG. 3 shows switching logic in accordance with one embodiment of the present disclosure.

FIG. 3 shows an example of switching logic 300 used to operate the switches 202, 204, 206, 208. In this case, the switching logic includes a set of two non-overlapping digital signals denoted as $\phi_1$ and $\phi_2$. The switches 202, 204, 206, 208 are divided into two sets. The first signal $\phi_1$ operates a first set of switches 202 and 206, while the second signal $\phi_2$ operates a second set of switches 204 and 208. The switching logic often includes a period of positive current (or negative current) produced by turning a set of switches "on" followed by a period of no current produced by turning the switches "off." In various embodiments, the switching logic alternates between the first set of switches and the second set of switches, as shown in FIG. 3, and, in this manner, produces an alternating positive and negative current within the coil 102. Repeating the switching logic at a given frequency generates radio frequency pulses and NMR pulse sequences at a particular frequency. The positive current generates the positive portions of the radio frequency pulses, while the negative current generates the negative portions of the radio frequency pulses.

The transmitter 104 also includes a driver 112 that is coupled to the transmitter circuit 110 and used to control operation of the switches 202, 204, 206, 208 within the transmitter circuit according to a switching logic. In one particular embodiment, the driver 112 is a computer processor. Each switch 202, 204, 206, 208 is coupled to the driver 102 so that the driver can control the operation of the switches. The driver 112 switches the switches 202, 204, 206, 208 according to the switching logic (e.g., $\phi_1$ and $\phi_2$). In various embodiments, the driver 112 also receives NMR pulse sequences from an NMR spectrometer 108. In some embodiments, the NMR pulse sequences are sent along a plurality of channels. An adder circuit (not shown) can be used to combine the plurality of channels. Also, in various embodiments, the transmitter 104 includes a comparator 114 for receiving the NMR pulse sequences from the spectrometer 108 and generating a square waveform that is provided to the driver 112. The NMR pulse sequences can be translated by the driver 112 into the particular switching logic by selecting waveforms of the NMR pulse sequences and then conditioning the waveforms to an appropriate voltage.

The addition of the capacitor 212 to the transmitter circuit 110 corrects or improves the power factor of the circuit. The power factor is a measure of the efficiency of the transmitter circuit. The power factor can be determined according to the following relationship:

$$\text{Power Factor} = \frac{P}{S}, \quad (2)$$

where S is the apparent power and P is the actual power. The apparent power (S) is the product of the average voltage and the average current within the coil 102, while the actual power (P) is the real power dissipated by the resistive load of the coil. When the power source directly powers the coil, the inductive load of the coil 102 causes a large phase difference between the current and the voltage within the coil so that the apparent power (S) is much larger than the actual power (P) dissipated in the resistive load of the coil. Thus, in such an arrangement, the power factor is low and the power source delivers a much greater amount of power than is actually dissipated by the coil. The addition of the capacitor 202 increases the power factor of the transmitter circuit 110. The capacitor 202 temporarily stores charge and provides charge to the coil 102 to level the current used by the coil during the discharging mode and charging mode.

Therefore, the amount of power delivered by the power source 210 will be closer to the actual power dissipated by the coil 102. This means that, in many cases, the transmitter circuit 110 reduces power draw from the power source 210 and the circuit can use a power source with reduced power specifications (e.g., lower voltage and current specifications). A non-resonant transmitter circuit with power factor correction is particularly beneficial in NMR wellbore applications, which have power constraints.

Figure 4:
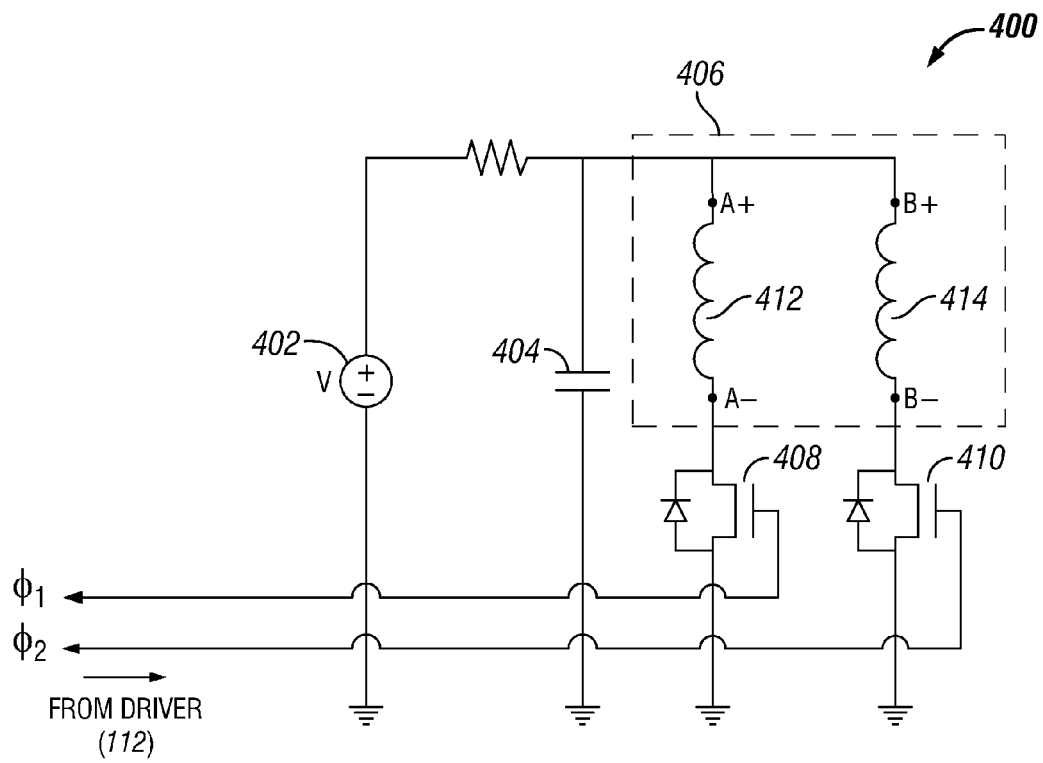
FIG. 4 shows a transmitter circuit in accordance with another embodiment of the present disclosure.

Illustrative embodiments of the present disclosure are not limited to any particular non-resonant transmitter circuit configuration. Non-resonant transmitter circuits that use other configurations are also within the scope of the present disclosure. For example, FIG. 4 shows a non-resonant transmitter circuit 400 in accordance with another embodiment of the present disclosure. The NMR transmitter circuit 400 includes a power supply 402, a capacitor 404, a coil 406, and two switches 408, 410 that selectively couple and decouple the capacitor 404 with the coil 406. Similarly to the non-resonant transmitter circuit 110 shown in FIG. 2, in this embodiment, the capacitor 404 is used to provide current to the coil 406 during radio frequency pulse generation and, in so doing, to correct the power factor of the transmitter circuit 400.

Figure 5:
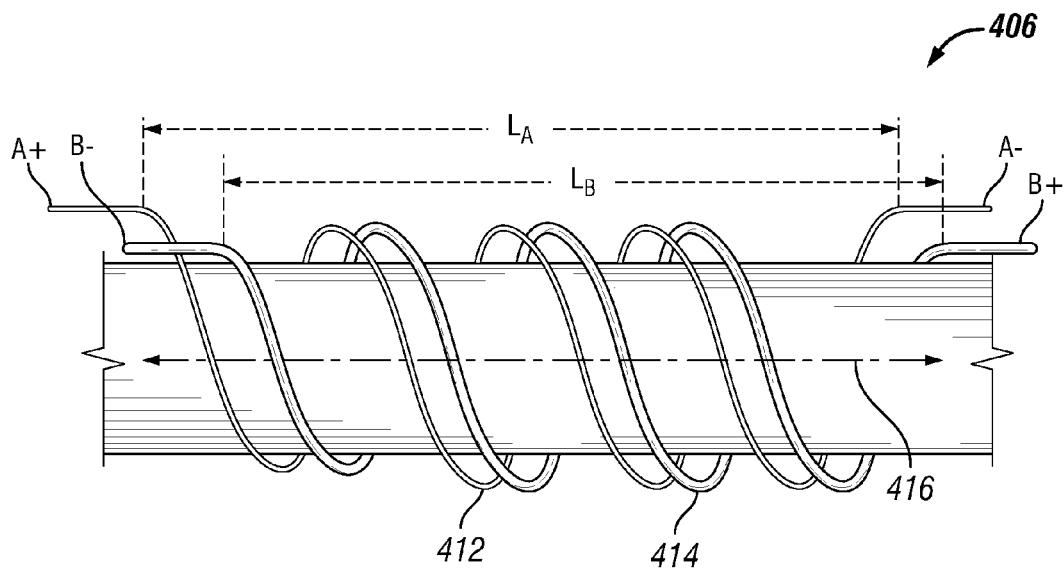
FIG. 5 shows a coil in accordance with one embodiment of the present disclosure.

FIG. 5 shows a detailed view of the coil 406 that is coupled to the transmitter circuit 400. The coil 406 includes a first coil section 412 and a second coil section 414 that pass current in opposite polarity. Each coil section 412, 414 includes a plurality of windings with winding lengths $L_A$ and $L_B$ along the longitudinal axis 416 of the coil 406. The winding lengths overlap along the length of the longitudinal axis 416. The first coil section 412 includes connections A+ and A− at its ends, while the second coil section 414 includes connections B+ and B− at its ends. The coil sections 412, 414 are connected to the transmitter circuit 400 in opposite polarity, as shown in FIG. 5, so that current passes through each coil section in opposite directions.

Each coil section 412, 414 is selectively powered by the switches 408, 410. To this end, the first switch 408 is coupled to a first coil section 412 and configured to selectively power the first coil section. The second switch 410 is coupled to the second coil section 414 and configured to selectively power the second coil section. Each switch and corresponding coil section is arranged in parallel. In one particular embodiment, the switches 408, 410 are transistors, such as any of the transistors described above.

Similarly to the non-resonant transmitter circuit 110 shown in FIG. 2, the non-resonant transmitter circuit 400 operates in a charging mode and discharging mode. In a charging mode, the switches 408, 410 are "off" and the power source 402 charges the capacitor 404 by providing current to the capacitor. In a discharging mode, the switches 408, 410, selectively couple and decouple the capacitor 404 with the coil sections 412, 414 by rapidly switching from "on" and "off" positions. As explained above, the capacitor 404 improves the power factor of the circuit by leveling the current used by the coil 406 during the discharging mode and charging mode.

By selectively coupling and decoupling each coil section 412, 414 with the capacitor 404, the switches 408, 410 control the timing of current flow within each section of the coil 406. Turning these switches 408, 410 on and off using a certain switching logic generates a pattern of current in the coil 406. The switching logic often includes a period of current produced by turning a switch "on" followed by a period of no current produced by turning the switch "off." In various embodiments, the switching logic alternates between injection of current into each coil section 412, 414 so that an alternating positive and negative current is generated within the coil 406. In this manner, the operation of the switches 408, 410 generates radio frequency pulses and the NMR pulse sequences. Further details of the transmitter circuit and coil arrangement shown in FIGS. 4 and 5 are provided in U.S. patent application Ser. No. 13/963,826 filed on Aug. 9, 2013, which is hereby incorporated by reference in its entirety.

In another illustrative embodiment, the transmitter circuit uses a plurality of capacitors to improve the power factor of the circuit. For example, the transmitter circuit includes a plurality of switches and a plurality of capacitors. Each switch is coupled to a separate capacitor. Each capacitor is responsible for providing the coil with current when the capacitor's respective switch is turned on and each capacitor is charged when the capacitor's respective switch is turned off.

Illustrative embodiments of the NMR transmitter and transmitter circuit described herein can switch between frequencies that are outside a natural resonant frequency bandwidth of a coil with a tuned circuit. Although the non-resonant transmitter circuit and coil use a capacitor and the circuit has some associated capacitance, this capacitance is not specifically selected to match a Larmor frequency of interest. In other words, the NMR transmitter does not depend on tuning a coil to set a particular pulse frequency. In contrast to narrowband systems, which use mechanical switches and banks of fixed capacitors to tune the coil to a Larmor frequency of interest according to equation 1 above, various embodiments of the transmitters described herein achieve multi-frequency operation without a need for hardware modulation (e.g., switching between fixed capacitors or tuning between variable capacitors). Instead, by rapidly turning a number of switches "on" and "off," the non-resonant transmitter circuit produces a waveform of a given frequency that is provided to the coil to generate radio frequency pulses. The frequency of the waveform can be modulated by operation of the switches. Thus, the NMR transmitter is frequency insensitive and allows the pulse frequency to be dynamically varied by the spectrometer while maintaining phase coherence of an output waveform. In some cases, the transmitter and transmitter circuit can switch between frequencies with a frequency difference as great as 10% of an initial applied frequency. In various other embodiments, the frequency can be even greater (e.g., 20% 30% or 50%). Also, in some embodiments, the transmitter and transmitter circuit can switch between frequencies in less than 5 µs. In yet further embodiments, the transmitter can switch between frequencies in less than 20 µs or 50 µs. Furthermore, in some embodiments, the transmitter and transmitter circuit can operate within a frequency range of 100 kHz and 3.2 MHz.

Figure 6:
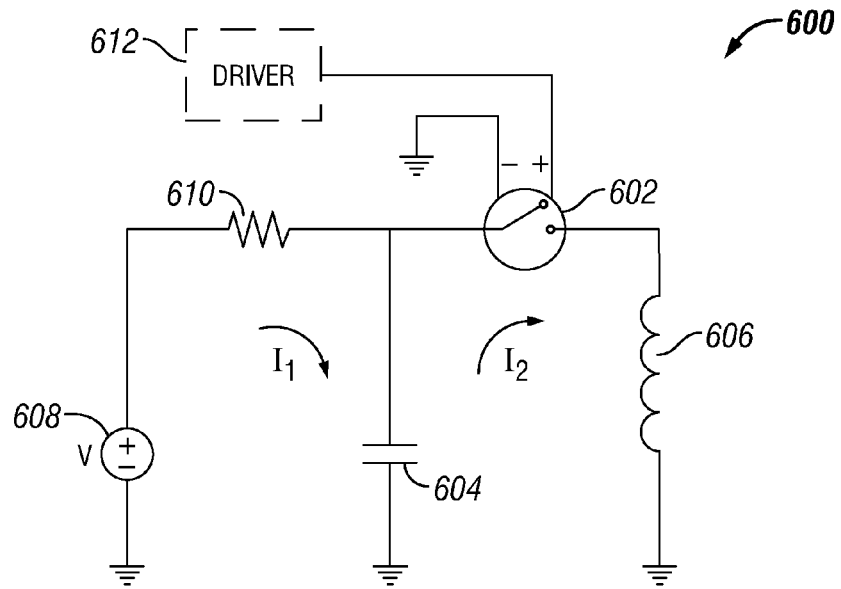
FIG. 6 shows a simplified transmitter circuit in accordance with one embodiment of the present disclosure.

FIG. 6 shows a simplified transmitter circuit 600 in accordance with one embodiment of the present disclosure. This simplified transmitter circuit 600 also operates in a charging mode and a discharging mode. Thus, the simplified transmitter circuit 600 operates in a similar manner to the transmitter circuits shown in FIGS. 2 and 4. In this embodiment, however, the simplified transmitter circuit 600 includes a single switch 602 that is coupled between a capacitor 604 and a coil 606. This simplified transmitter circuit 600 is used as an example to more easily demonstrate the operation of the non-resonant transmitter circuits described herein.

Equations 3 to 11 below can be used to model the performance of the simplified transmitter circuit 600 as well as other transmitter circuits that use a plurality of switches, such as those shown in FIGS. 2 and 4. Like those other circuits, in the charging mode, the switch 602 of the simplified circuit 600 is open and a power source 608 charges the capacitor 604 according to a time constant. The time constant can be obtained by multiplying the resistance of resistor 610 ($R_1$) and the capacitance of the capacitor 604 ($C_1$). The current in a first loop of the transmitter circuit 600 ($I_1$) can be obtained according to the following relationship:

$$I_1 = \frac{V}{R_1 \exp\left(\frac{-t}{RC_1}\right)}, \quad (3)$$

where V is the voltage output by the power source 608, $C_1$ is the capacitance of the capacitor 604, $R_1$ is the resistance of the resistor 610, and R is the resistance of the coil 606.

The voltage at the capacitor 604 ($V_1$) can be obtained according to the following relationship:

$$V_1 = V\left[1 - \exp\left(\frac{-t}{RC_1}\right)\right]. \quad (4)$$

In the discharging mode, the switch 602 rapidly opens and closes to generate a radio frequency pulse and the coil 606 draws current from the capacitor 604. The energy drawn from the capacitor 604 is small compared to the energy stored within the capacitor so that the voltage on capacitor remains constant during the discharging mode. The energy dissipation from the capacitor 604 due to resistive loss at the coil 606 during the discharging mode ($E_r$) can be obtained from the following relationship:

$$E_r = \tfrac{1}{2} I_2^2 R T_p. \quad (5)$$

where $I_2$ is the current in the second loop, R is the resistance of the coil, and $T_p$ is the length of the radio frequency pulse, which corresponds to the discharging time period.

The energy stored in the capacitor 604 ($E_1$) can be determined according to the following relationship:

$$E_1 = \tfrac{1}{2} V^2 C_1. \quad (6)$$

The energy stored in the coil 606 during the charging mode ($E_L$) can be determined according to the following relationship:

$$E_L = \tfrac{1}{2} L I_2^2. \quad (7)$$

Assuming the discharging mode dissipates all of the energy in the switch 602, the total energy used during the discharging mode ($E_p$) can be determined according to the following relationship:

$$E_p = 2 T_p f E_L = T_p f L I_2^2, \quad (8)$$

where f is the operating frequency of the switch 606, which may correspond to the frequency of the radio frequency pulse (e.g., the Larmor frequency). For a transmitter circuit with a plurality of switches, such as the ones in FIGS. 2 and 4, the duty cycle is doubled because different switches are responsible for generating the positive and negative portions of the radio frequency pulse.

The incremental decrease of the voltage at the capacitor 604 (ΔV), due to a number of radio frequency pulses, can be obtained according to the following relationship:

$$\Delta V \sim \frac{E_p + E_r}{VC_1} \quad (9)$$

The charging current ($I_c$) that is sufficient to replenish the capacitor 604, due to the energy loss during the time of the radio frequency pulse and echoes, can be obtained according to the following relationship:

$$I_c = \frac{E_p + E_r}{VT_e} \sim \frac{T_p}{\pi T_e} I_2, \quad (10)$$

where $T_e$ is the length of the delay time, which corresponds to the time between radio frequency pulses and the charging time period. The delay time may also correspond to an echo time. The echo time is used to set the position of echoes in the NMR signal.

Equation 10 can be used to describe the behavior of the transmitter circuit 600 when the coil has a Q factor that is greater than 1. In such a case, the energy loss ($E_r$) during the radio frequency pulse is smaller than the energy stored in the coil 606 ($E_p \sim QE_r > E_r$). Furthermore, equation 10 can be used to describe the behavior of the transmitter circuit 600 when the capacitance of the capacitor 604 ($C_1$) is larger than the resonant capacitance of the coil 606. The resonant capacitance of the coil 606 ($C_0$) can be obtained according to the following relationship:

$$C_0 \equiv \frac{1}{4\pi^2 f^2 L} \quad (11)$$

If the capacitor 604 is smaller than the resonant capacitance of the coil ($C_0$), then the capacitor will not function as charge storage for generation of radio frequency pulses. To avoid this scenario, in illustrative embodiments, the capacitor 604 is sufficiently large so that the capacitor can store enough charge for at least one radio frequency pulse over its length ($T_p$). To this end, the capacitor 604 is at least as large as the resonant capacitance of the coil 606. In further illustrative embodiments, the capacitor 604 is much larger than the resonant capacitance of the coil 606. For example, the capacitor 604 may be larger than the resonant capacitance of the coil 606 by at least a factor of 2.

The capacitor 604 is used as a temporary storage of charge in order to level (e.g., smooth out) the current used by the coil 606 during the discharging mode and charging mode. As a result, the power supply can provide an average current that is reduced from the peak requirement of the coil by a factor of $T_p/T_e$. For a NMR system that uses a radio frequency pulse ($T_p$) of about 50 μs and a delay time ($T_e$) of about 500 μs, the average current is reduced by a factor of 10.

In one specific example, the transmitter circuit 600 includes a coil 606 with an inductance (L) of 20 μH and a series resistance (R) of 1.0 ohms, a capacitor 604 with a capacitance ($C_1$) of 1 μF, a voltage output by the power source 608 (V) of 1000 V, and an operating frequency (f) of 250 kHz. The equations above can be used to calculate various electrical properties of the transmitter circuit 600.

Those properties are presented below in Table 1. In this specific example, the average apparent power supplied by the power source 608 is between 220 and 640 W and is much smaller than a peak requirement for the coil 606 alone of 20 kW.

TABLE 1

| | |
|---|---|
| Resistive loss at the coil ($E_r$) | 0.01 J |
| Stored energy in the capacitor ($E_l$) | 0.5 J |
| Energy loss ($E_p$) | 0.1 J |
| Incremental decrease of voltage (ΔV) | 110 V |
| Charging current ($I_c$) | 0.22 A |
| $\frac{T_p}{T_e \pi} I_2$ | 0.64 A |
| Resonant capacitance ($C_0$) | 20 nF |
| Apparent charging power | 220-640 W |

Equations 3-11 above are simplified in order to explain the operation of the non-resonant transmitter circuits described herein. These equations do not account for the time-dependence of voltage and current during the charging and discharging modes. Also, these equations assume that the charging of the capacitor 604 during the discharging mode is insubstantial. Operation of the non-resonant transmitter circuits described herein is not limited to the behavior defined by these equations.

FIGS. 7-10 were generated by simulating the simplified transmitter circuit 600, as shown in FIG. 6, using conventional simulation software. Table 2 below shows parameters for each component within the circuit 600.

TABLE 2

| | |
|---|---|
| Power supply 608 (V) | Constant 500 V |
| Resistor 610 ($R_1$) | 20 ohm |
| Capacitor 604 ($C_1$) | 3 μF |
| Coil 606 inductance (L) | 20 μH |
| Coil 606 and substance resistance (R) | 5 ohm |
| Driver 612 | The driver is simulated as a power supply that supplies a "saw tooth" waveform at 0 and 1 V. Each "radio frequency pulse" includes 20 saw tooth waveforms. Each tooth has a duration of 2 μs to generate a radio frequency of 0.25 MHz. |
| Switch 602 | A voltage controlled switch: on-resistance = 1 ohm; off-resistance = 1 Mohm; and the switch turns at 0.5 V. |

Figure 7:
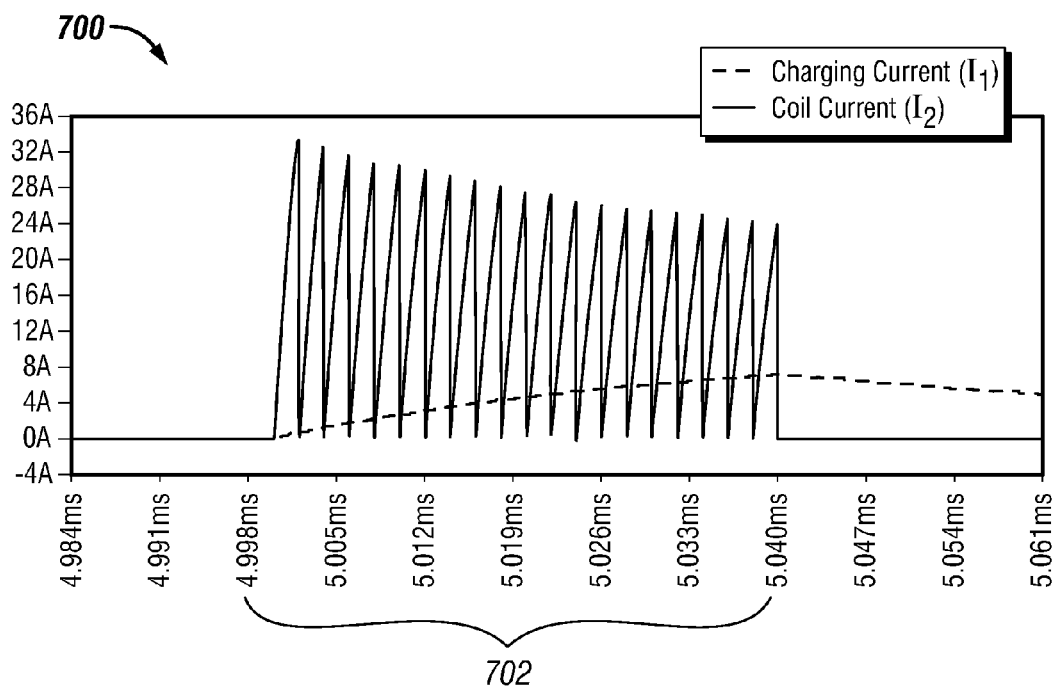
FIG. 7 shows a plot of current versus time for charging current ($I_1$) and coil current ($I_2$) during operation of the simplified transmitter circuit in accordance with one embodiment of the present disclosure.

FIG. 7 shows a plot 700 of current versus time for charging current ($I_1$) (e.g., current in the first loop) and coil current ($I_2$) (e.g., current in the second loop) during generation of a radio frequency pulse 702 by the simplified transmitter circuit 600. The plot 700 shows that a supply voltage (V) of 500 V can produce a coil current ($I_2$) in excess of 20 A with a smaller charging current ($I_2$). As the radio frequency pulse is applied, the coil current ($I_2$) drops from 33 A to 24 A. This drop is due to the corresponding voltage drop on the capacitor 604, as shown in FIG. 8.

Figure 8:
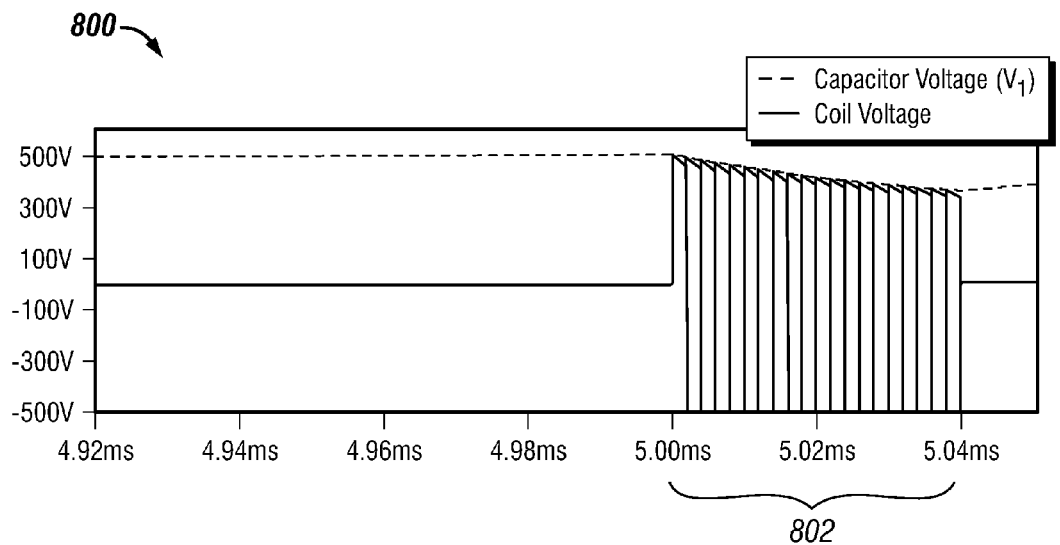
FIG. 8 shows a plot of voltage versus time for capacitor voltage ($V_1$) and coil voltage during operation of the simplified transmitter circuit in accordance with one embodiment of the present disclosure.

FIG. 8 shows a plot 800 of voltage versus time for capacitor voltage ($V_1$) (e.g., voltage at the capacitor 604) and coil voltage (e.g., voltage at the coil 606) during generation of a radio frequency pulse 802 by the simplified transmitter circuit 600. The capacitor voltage ($V_1$) drops during generation of the radio frequency pulse. The coil voltage approximately follows the drop of the capacitor voltage ($V_1$), which means that the coil current ($I_2$) will also drop as the pulse is applied. The coil voltage also shows a large negative voltage at the end of each saw tooth wave form. This large negative voltage appears because the switch simulation 602 does not account for the capacitance and the diode in a typical field effect transistor switch.

Figure 9:
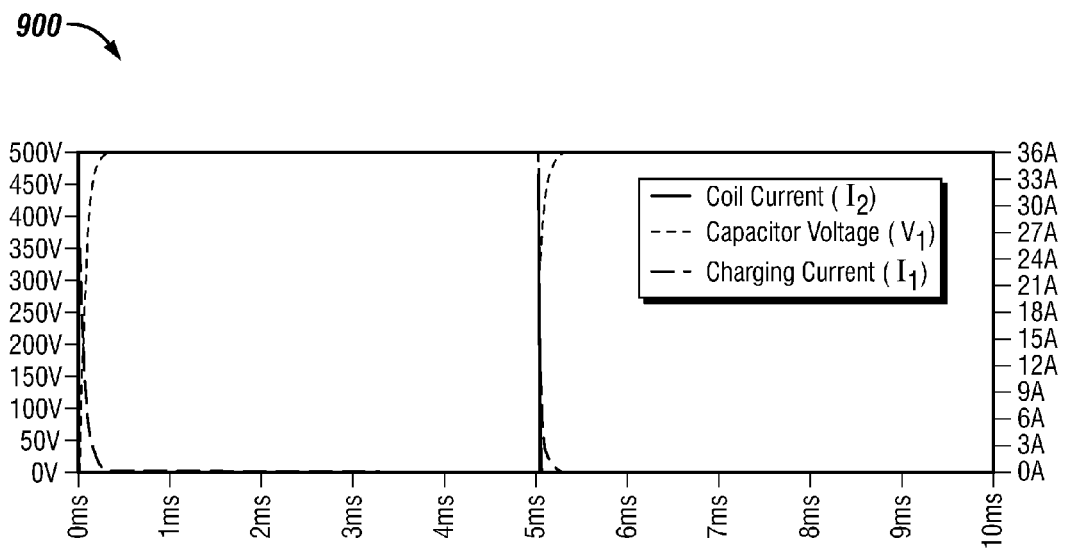
FIG. 9 shows a plot of voltage and current versus time for charging current ($I_1$), coil current ($I_2$), and capacitor voltage ($V_1$) during charging of a capacitor and generation of a radio frequency pulse by the simplified transmitter circuit in accordance with one embodiment of the present disclosure.

FIG. 9 shows a plot 900 of voltage and current versus time for charging current (I$_1$), coil current (I$_2$), and capacitor voltage (V$_1$) during charging of the capacitor 604 and generation of a radio frequency pulse. At 0.0 ms, the capacitor 604 begins charging and, at 5 ms, a radio frequency pulse is generated. The plot 900 shows that the capacitor 604 provides for a charging current (I$_1$) that is significantly smaller than the coil current (I$_2$). The smaller charging current (I$_1$), in turn, reduces the power draw from the power supply 608. The average current during the charging cycle (0.0-0.5 ms) is approximately 1.3 A and the average charging power is 800 W. The plot also shows that the charging current has a peak of approximately 7 A, which is substantial. This peak is due to the use of a constant source impedance (e.g., resistor 610=20 ohm). An increase in the resistance of the resistor 610 will reduce the peak current and lengthen the charging time.

Figure 10:
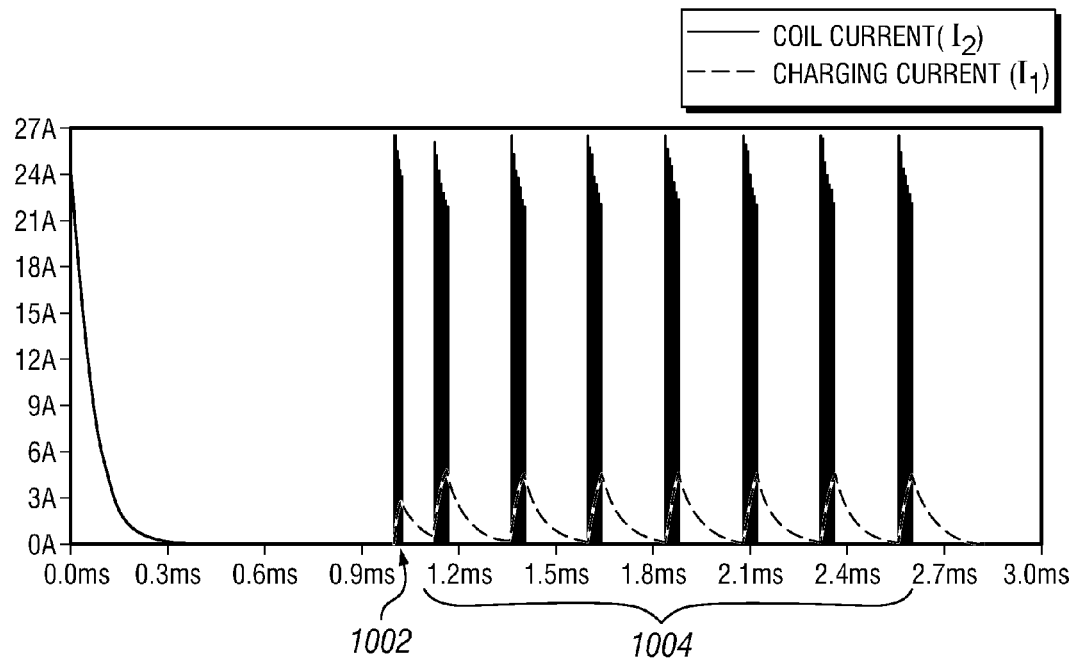
FIG. 10 shows a plot of current versus time for charging current ($I_1$) and coil current ($I_2$) during application of a Carr, Purcell, Meiboom and Gill (CPMG) sequence by the simplified transmitter circuit in accordance with one embodiment of the present disclosure.

FIG. 10 shows a plot 1000 of current versus time for charging current (I$_1$) and coil current (I$_2$) during application of a Carr, Purcell, Meiboom and Gill (CPMG) sequence. The CPMG sequence includes an excitation radio frequency pulse 1002 followed by a series of refocusing pulses 1004. The delay time between each refocusing pulse is 200 μs. The plot shows that the transmitter circuit 600 can be used to apply the CPMG sequence. More specifically, there is sufficient time to charge the capacitor 604 during the delay time.

Operation of the non-resonant transmitter circuits described herein is not limited to the characteristics and behaviors shown in FIGS. 7-10, which were generated using the simplified transmitter circuit 600.

Figure 11:
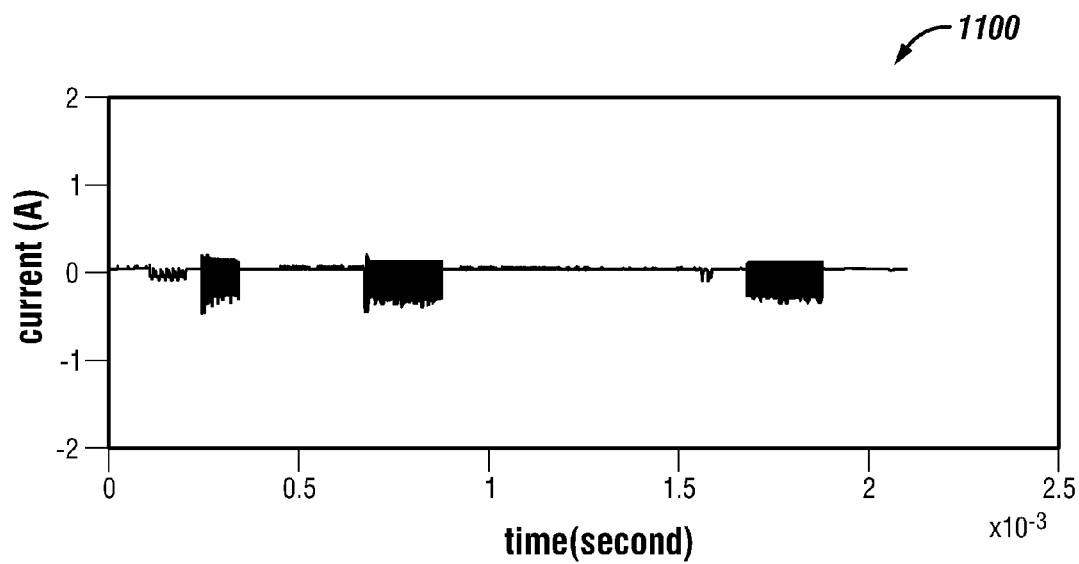
FIG. 11 shows a plot of current versus time for charging current ($I_1$) during application of a CPMG sequence in accordance with one embodiment of the present disclosure.
Figure 12:
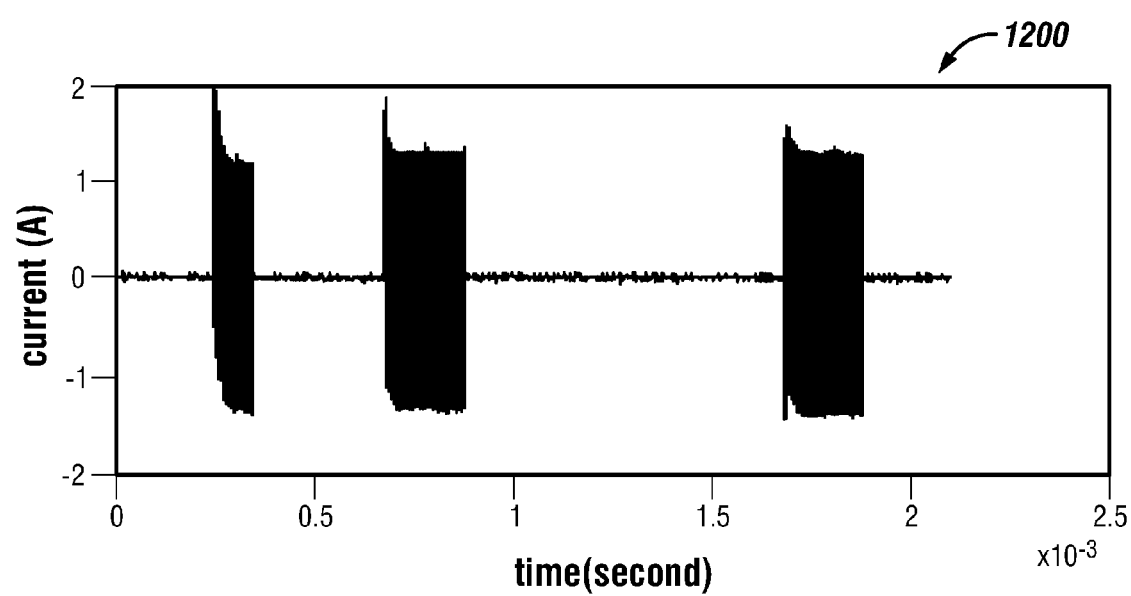
FIG. 12 show a plot of current versus time for coil current ($I_2$) during application of the CPMG sequence in accordance with one embodiment of the present disclosure.

FIGS. 11 and 12 were generated using the NMR transmitter 104 shown in FIG. 1 and the transmitter circuit 110 shown in FIG. 2. In the transmitter circuit 110, the power source 210 was a DC power supply with a 60 V maximum voltage, a 3 A maximum current, and a bandwidth of approximately 11 kHz. The internal resistance of the power supply was less than 2 mohms and the power supply had an output inductance of approximately 2 mH. The capacitor 212 within the transmitter circuit 212 was a 10 μF electrolytic capacitor rated to 100 V. The coil 102 had an inductance of 15 pH and a Q factor of about 60 at 500 kHz. The transmitter circuit 110 included four N-channel MOSFETs transistors that were integrated into a single chip.

The NMR transmitter 104 and the transmitter circuit 110 applied a CPMG sequence with 180-degree pulses that were separated by a 1 ms delay time. The pulses were applied at 500 kHz and were 200 μs in duration. The power source 210 was set to 50 V during application of the CPMG sequence. The charging current (I$_1$) and the coil current (I$_2$) generated during application of the CPMG sequence were measured using a current probe at the connection to the power source and at the coil lead. The waveforms detected by the current probe were recorded by an oscilloscope.

FIGS. 11 and 12 show plots of current versus time for charging current (I$_1$) 1100 and coil current (I$_2$) 1200 during the CPMG sequence. During the pulses, the charging current (I$_1$) is approximately 0.25 A, while the coil current is approximately 2.5 A. Thus, the plots show that the charging capacitor 212 reduces the current requirement of the power source 210 by a factor of 10.

Referring back to FIG. 1, the coil 102 is also coupled to a NMR receiver 106 so that NMR resonant signals that are generated within the substance 101 can be detected, amplified, and analyzed. In one specific embodiment, the receiver 106 is a broadband NMR receiver, which can receive and process resonant NMR signals over a broad frequency range. The coil 102 is coupled to the receiver 106 using a duplexer 116. The duplexer 116 decouples the receiver 106 from the coil 102 when the coil is operating in a transmitting mode (e.g., transmitting an NMR pulse sequence). In one particular embodiment, the duplexer 116 includes switches and a switch driver 118 that opens the switches during a transmitting mode and closes the switches during a receiving mode of operation. In this manner, the duplexer 116 protects the receiver 106 during a transmitting mode. A duplexer may not be used when the NMR system 100 includes separate transmit and receive coils.

The NMR system 100 also includes a spectrometer 108 that is used to provide NMR pulse sequences to the NMR transmitter 104 and to analyze the NMR signal received from the NMR receiver 106. In various embodiments, the detected NMR signal is output by the NMR receiver 106 in analog form. In such embodiments, the spectrometer 108 may include a digitizer 120 (e.g., analog-to-digital converter) for converting the detected NMR signal into digital data. Furthermore, in various embodiments, demodulation of the NMR signal can occur within the spectrometer 108. In various other embodiments, however, demodulation of the NMR signal can also occur within the NMR receiver 106. The spectrometer 108 also includes a post-processor 122 that is used to interpret the detected digital NMR data and to determine NMR properties from the detected data. This data can be presented to a user using an operator interface with a graphical user interface (GUI). The spectrometer 108 also includes a pulse sequence generator 124 that generates NMR pulse sequences based upon parameters selected by an operator at the operator interface. The pulse sequence generator provides the sequences to the NMR transmitter 104. In one particular embodiment, the spectrometer 108 is a KEA™, which can be obtained from Magritek of Wellington, NZ. The spectrometer 108 can be controlled from the operator interface using PROSPA™ software, which can also be obtained from Magritek.

Further details of NMR electronics, NMR transmitters, and NMR receivers are described in U.S. Publication No. 2012/0001629 published on Jan. 5, 2012; U.S. application Ser. No. 13/774,457 filed on Feb. 22, 2013; and U.S. patent application Ser. No. 13/963,826 filed on Aug. 9, 2013, each of which is incorporated by reference in their entireties.

As shown in FIG. 1, the NMR system 100 includes an electro-magnetic device 126 for applying a static magnetic field to the substance 101. In some embodiments, the electro-magnetic device 126 is a magnet or an array of magnets. The magnets can be formed from a samarium-cobalt (SmCo) magnetic material.

The NMR system 100 also includes an operator interface 128 for communicating with the spectrometer 108. The operator interface 128 includes a computer system. The computer system may include a computer processor 130 (e.g., a microprocessor, microcontroller, digital signal processor, or general purpose computer) for executing any of the methods and processes described herein. The computer system may further include a memory 132 such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The memory 132 can be used to store computer instructions (e.g., computer program code) that are interpreted and executed by the processor 130.

NMR pulse sequences may be implemented as a series of computer instructions (e.g., software or firmware) fixed on a non-transitory tangible medium, such as a computer readable medium (e.g., a memory), or transmittable to the computer system, via a modem or other interface device, such as a communications adapter connected to a network over a tangible medium (e.g., optical or analog communications lines). The series of computer instructions can embody all or part of the NMR pulse sequences. The processor 130 may be configured to retrieve the sequences from the memory 132 and provide instructions to the NMR electronics 104, 106, 108 to apply the sequences to the substance 101. The detected resonant signals may also be communicated from the NMR electronics 104, 106, 108 to the processor 130 for storage on the memory 132.

The operator interface 128 also supports the graphical user interface 134 (GUI) (e.g., a monitor, a touch screen, a mouse, a keyboard and/or a joystick). The GUI 134 allows an operator to control and communicate with the NMR electronics 104, 106, 108. In various embodiments, the operator interface 128 can be used to perform functions selected from the following non-limiting list:

Communicate NMR pulse sequences from the operator interface 128 to the NMR electronics 104, 106, 108;

Communicate instructions to the NMR electronics 104, 106, 108 to initiate and/or terminate NMR measurements;

Communicate instructions to change parameters of NMR pulse sequences to the NMR electronics 104, 106, 108 (e.g., pulse amplitude of sequences, pulse lengths, timing between pulses, shape of pulses, and/or frequency of pulses);

Communicate detected NMR signal data from the NMR electronics 104, 106, 108 to the operator interface 128;

Perform analysis at the operator interface 128 of detected NMR signal data to determine NMR properties of substances; and Display various plots of NMR properties to the operator at the operator interface 128.

Illustrative embodiments of the present disclosure are not limited to the NMR system 100 shown in FIG. 1. Various modifications can be made to the system. For example, in one specific embodiment, the NMR electronics 104, 106, 108 include an additional computer system that supports the NMR electronics. In such an embodiment, the NMR electronics 104, 106, 108 and operator interface 128 may include their own communication modules, which provide for communication between the NMR electronics and the operator interface. A communications link between the communication modules can be established using, for example, a hard-wired link, an optical link, acoustic link, and/or a wireless link. By using the communication modules, the NMR electronics 104, 106, 108 and the operator interface 128 can be physically located in two separate locations. For example, in a wellbore application, the NMR electronics 104, 106, 108 can be located downhole, while the operator interface 128 is located at the surface.

Figure 13:
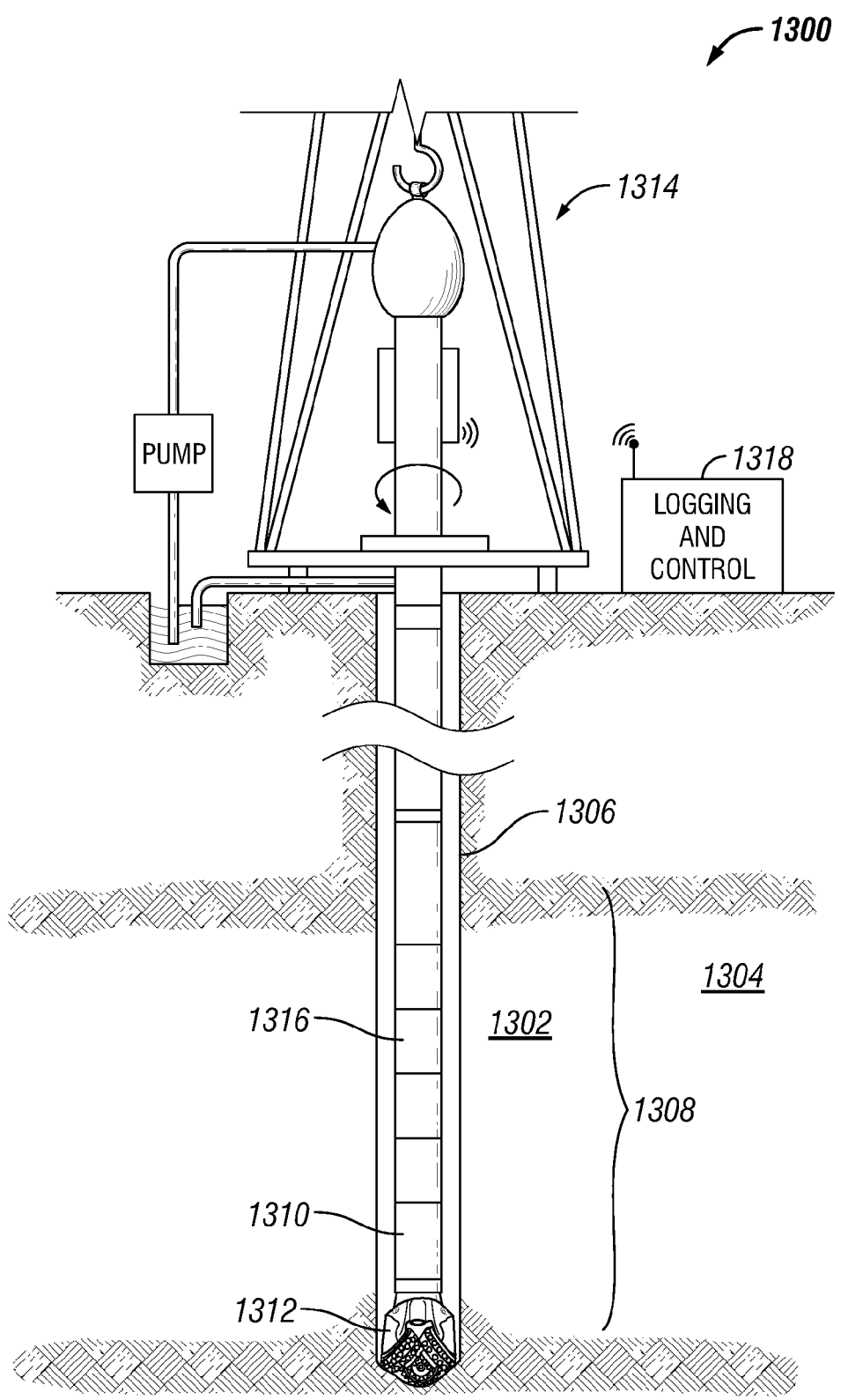
FIG. 13 shows a logging-while-drilling (LWD) system in accordance with one embodiment of the present disclosure.

Illustrative embodiments of the present disclosure are further directed to oil and gas field applications, such as wellbore logging tools. In particular, FIG. 13 shows a logging-while-drilling (LWD) system 1300 for investigating, in situ, a substance 1302 within an earth formation 1304 and determining a property of the substance, while a drilling operation is performed. The LWD system 1300 includes a drill string 1308 that is disposed within a wellbore 1306 that traverses the formation 1304. The drill string 1308 includes a drill collar 1310 with a drill bit 1312 disposed at the lower-end of the drill collar. The LWD system 1300 also includes a surface system with a derrick assembly and platform assembly 1314 positioned over the wellbore 1306. The derrick assembly 1314 rotates the drill string 1308 and, as the drill string rotates, the drill bit 1312 drills deeper into the wellbore 1306. An LWD NMR logging module 1316 is disposed within the drill collar 1310 so that the module can log the surrounding earth formation as the drilling operation is performed. The logging module 1316 communicates with surface equipment 1318, which includes an operator interface for communicating with the module. Such an operator interface has already been described with reference to FIG. 1. In various embodiments, the NMR logging module 1316 and operator interface can communicate via any one of a wired-drill pipe connection, an acoustic telemetry connection, optical communication and/or electronic communication.

Figure 14:
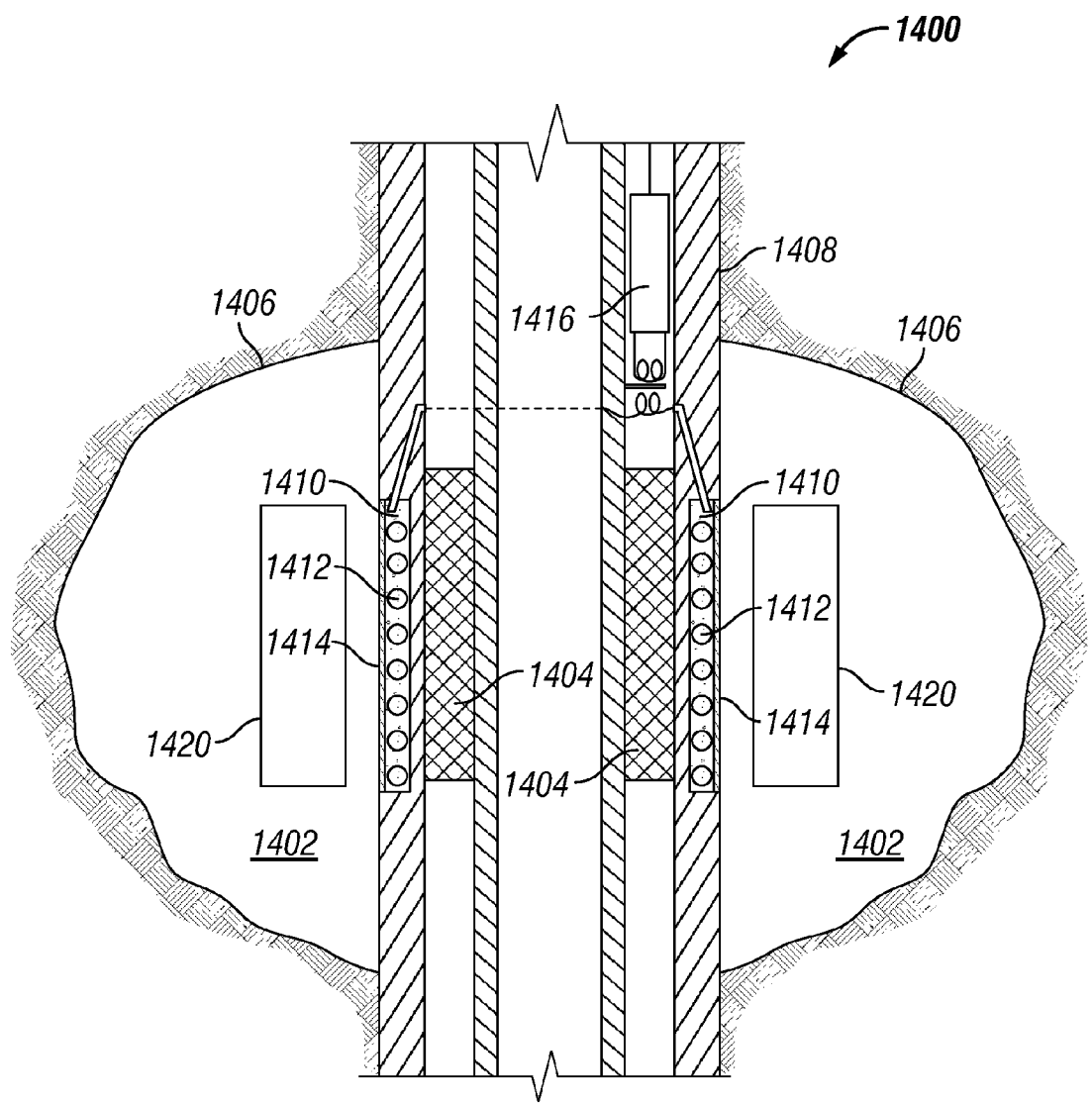
FIG. 14 shows a LWD NMR logging module in accordance with one embodiment of the present disclosure.

FIG. 14 shows an LWD NMR logging module 1400 for applying NMR pulse sequences to the formation. The module 1400 includes magnet sections 1404 that generate a static magnetic field within a zone of sensitivity 1406 within the formation 1402. The module 1400 also includes a drill collar 1408 with an axial slot 1410. A coil 1412 is disposed within the axial slot 1410 and the slot is filled with an insulator, such as ceramic, epoxy, or fiberglass. The coil 1412 is wound around the drill collar 1408 within the axial slot 1410. The axial slot 1410 is sealed using a cover 1414. In some embodiments, the cover 1414 is formed from a non-magnetic material and/or non-conductive material. At one end, the coil 1412 is grounded (e.g., to the drill collar 1408). At the other end, the coil 1412 is coupled to NMR electronics 1416, which include a transmitter with a non-resonant transmitter circuit, as described in, for example, FIG. 2 or 4. In some embodiments, the power source for the transmitter circuit is a turbine. The turbine charges the capacitor within the transmitter circuit and the capacitor, in turn, powers the coil 1412. As explained above, the capacitor improves the power factor of the transmitter circuit and makes the circuit particularly beneficial in NMR wellbore applications, which have power constraints. The NMR electronics 1416 are coupled to the coil 1412 via, for example, pressure feed-throughs. The coil 1412 applies an oscillating magnetic field (e.g., NMR pulse sequences) to an area of interest 1420 within the zone of sensitivity 1406 of the formation 1402. In some embodiments, the oscillating magnetic field is axially symmetric to facilitate measurements during rotation of the drill string. The coil 1412 also detects an NMR signal produced by the oscillating magnetic field within the formation. The NMR signal can be used to determine properties of the formation, such as a porosity of the formation and/or a bulk diffusion coefficient of formation fluids within the formation. Further details of NMR LWD systems are described in U.S. Pat. No. 5,629,623 issued on May 13, 1997 and U.S. Pat. No. 6,392,410, issued on May 21, 2002. Each of these patents is incorporated by reference herein in their entireties. One specific example of a NMR LWD tool is Schlumberger's proVISION™ tool.

Figure 15:
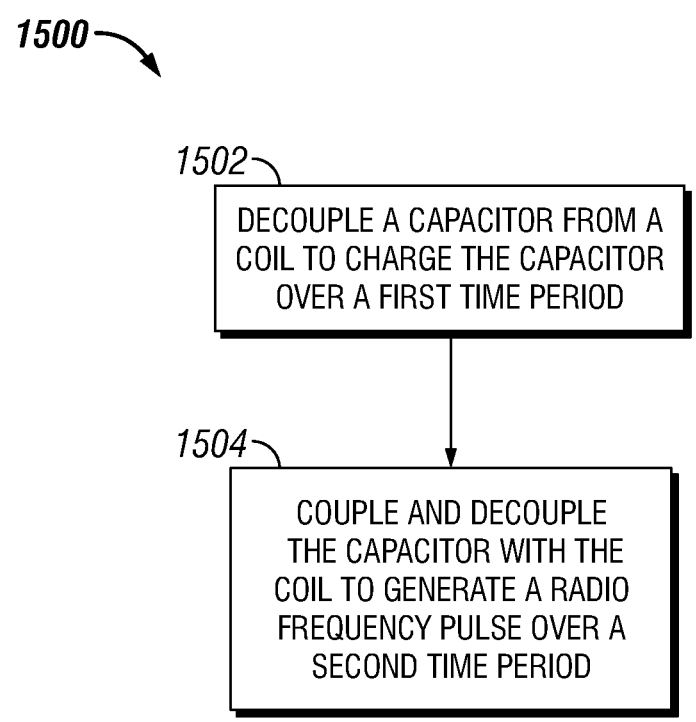
FIG. 15 shows a method for transmitting radio frequency pulses using a non-resonant transmitter in accordance with one embodiment of the present disclosure.

FIG. 15 shows a method 1500 for transmitting radio frequency pulses (e.g., NMR pulse sequences) using a non-resonant transmitter. The transmitter circuit includes a coil for transmitting radio frequency pulses and a capacitor for providing current to the coil. Before the method begins, a substance can be placed within or near the coil for evaluation. At process 1502, the coil is decoupled from the capacitor to charge the capacitor over a charging time period. The charging time period may correspond to a delay time ($T_e$) between radio frequency pulses in a NMR pulse sequence. When the coil is decoupled from the capacitor, the coil is charged by a power source. At process 1502, the capacitor and the coil are coupled and decoupled to generate a radio frequency pulse over a discharging time period. The discharging time period corresponds to the temporal duration of the radio frequency pulse ($T_p$). By rapidly coupling and decoupling the capacitor and the coil a plurality of times, the method produces a current waveform of a given frequency that is provided to the coil to generate the radio frequency pulse. The coupling and decoupling of the capacitor and the coil can be performed by a number of switches (e.g., transistors). Processes 1502 and 1504 can be repeated a plurality of times to generate a plurality of radio frequency pulses that form an NMR pulse sequence. An NMR pulse sequence includes a series of such pulses of specific duration with delay times between adjacent pulses. The NMR pulse sequences may include, for example, a free-induction decay sequence, a spin echo sequence, a stimulated echo sequence, an inversion recovery sequence, a Carr, Purcell, Meiboom and Gill (CPMG) sequence, or some combination of such sequences. In some embodiments, the NMR signal generated within the substance is detected using the coil. The NMR signal is then used to determine a property of the substance, such as $T_1$ relaxation time, $T_2$ relaxation time, and attenuation of the signal due to molecular diffusion.

The NMR transmitters and coils described herein are not limited to any particular device type or system. The NMR transmitters and methods described herein can be implemented in surface environments, such as in a laboratory. The NMR transmitters can be used in chemical production, food production, material inspection, and infrastructure inspection (e.g., building and bridges).

The NMR systems and methods described herein are not limited to any particular wellbore application. The NMR systems and methods described herein can be used with LWD systems, such as the one shown in FIGS. 13 and 14. Also, the NMR systems and methods described herein can be applied to wireline systems (e.g., a wireline tool) or measuring-while-drilling systems (e.g., MWD tools). Illustrative embodiments can also be used with any suitable means of conveyance, such as armored cable or coiled tubing. Furthermore, the NMR transmitters and methods described herein can be used to investigate a substance within an earth formation outside the wellbore tool (e.g., outside the coil) or to investigate a substance within a flow line or chamber within a wellbore tool (e.g., inside the coil).

The NMR systems and methods described herein are not limited to implementing NMR techniques and sequences. The systems and devices described herein can also be used to implement other magnetic resonance (MR) techniques and sequences, such as nuclear quadrupole resonance (NQR) techniques and sequences.

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

What is claimed is:

1. A non-resonant magnetic resonance (MR) device for transmitting radio frequency pulses, the device comprising:
   a coil for transmitting the radio frequency pulses;
   a circuit configured to operate in a charging mode and a discharging mode, wherein the circuit comprises:
   a capacitor;
   a power source coupled to the capacitor; and
   at least one switch that selectively couples the coil to both the capacitor and the power source;
   wherein, in the charging mode, (i) the at least one switch decouples the coil from the capacitor and (ii) the power source charges the capacitor; and
   wherein, in the discharging mode, the at least one switch alternatingly (i) couples the coil to both the capacitor and the power source and (ii) decouples the coil from both the capacitor and the power source at a frequency selected to generate the radio frequency pulses.

2. The device of claim 1, wherein the capacitor comprises a capacitance of at least 1 pico-Farad.

3. The device of claim 1, wherein the capacitor and the power source power the coil when the at least one switch couples the coil to the capacitor.

4. The device of claim 1, wherein the circuit comprises a plurality of switches coupled between the capacitor and the coil and configured to selectively couple the coil to both the capacitor and the power source.

5. The device of claim 4, wherein the plurality of switches comprises transistors.

6. The device of claim 5, wherein the plurality of switches are arranged in an H-bridge.

7. The device of claim 5, further comprising:
   a driver coupled to the circuit and configured to control operation of the plurality of switches.

8. The device of claim 7, wherein the operation of the switches generates the radio frequency pulses.

9. The device of claim 1, wherein the device is part of a wellbore logging tool.

10. A method for transmitting radio frequency pulses, the method comprising:
    (i) decoupling a capacitor from a coil to charge the capacitor over a first time period using a power source; and
    (ii) alternatingly coupling the coil to both the capacitor and the power source and decoupling both the capacitor and the power source from with the coil to generate a radio frequency pulse over a second time period; wherein
    the coupling and decoupling of processes (i) and (ii) are performed using a plurality of switches.

11. The method of claim 10, wherein the coupling and decoupling in process (ii) comprises coupling and decoupling both the capacitor and the power source with the coil a plurality of times to generate the radio frequency pulse over the second time period.

12. The method of claim 11, further comprising repeating processes (i) and (ii) a plurality of times to generate a plurality of radio frequency pulses that are each separated from adjacent radio frequency pulses by respective instances of the first time period.

13. The method of claim 10, wherein the plurality of switches comprises a plurality of transistors.

14. The method of claim 10, further comprising applying the radio frequency pulse to a formation.

15. A non-resonant magnetic resonance (MR) device for transmitting radio frequency pulses, the device comprising:
    a coil for transmitting the radio frequency pulses;
    a circuit configured to operate in a charging mode and a discharging mode, wherein the circuit comprises:
    a capacitor arranged in parallel with the coil;
    a power source that is coupled to the capacitor; and a plurality of transistors coupled between the capacitor and the coil and configured to selectively couple the coil to both the capacitor and the power source; and wherein, in the charging mode, (i) the plurality of transistors decouple the coil from the capacitor and (ii) the power source charges the capacitor; and wherein, in the discharging mode, the plurality of transistors alternatingly (i) couple the coil to both the capacitor and the power source and (ii) decouple the coil from both the capacitor and the power source at a frequency selected to generate the radio frequency pulses.

16. The device of claim 15, wherein the capacitor comprises a capacitance of at least 1 pico-Farad.

17. The device of claim 15, further comprising:
a driver coupled to the circuit and configured to control operation of the plurality of transistors.

18. The device of claim 17, wherein operation of the transistors generates the radio frequency pulses.

19. The device of claim 15, wherein the device is part of a wellbore logging tool.

* * * * *